US010308950B2

(12) United States Patent
Chapman et al.

(10) Patent No.: US 10,308,950 B2
(45) Date of Patent: Jun. 4, 2019

(54) METHODS FOR INCREASING OIL CONTENT IN PLANT TISSUES BY SUPPRESSING HYDROPHOBIC LIPID DROPLET PROTEIN

(71) Applicants: University of North Texas, Denton, TX (US); The United States of America as represented by the Secretary of Agriculture, Washington, DC (US); Robert Mullen, Denton, TX (US); Michal Pyc, Denton, TX (US)

(72) Inventors: Kent Chapman, Denton, TX (US); Robert Mullen, Denton, TX (US); Michal Pyc, Denton, TX (US); John M. Dyer, Denton, TX (US)

(73) Assignees: University of North Texas, Denton, TX (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/624,495

(22) Filed: Jun. 15, 2017

(65) Prior Publication Data

US 2017/0362602 A1    Dec. 21, 2017

Related U.S. Application Data

(60) Provisional application No. 62/350,843, filed on Jun. 16, 2016.

(51) Int. Cl.
*C12N 15/82*     (2006.01)
*A01H 5/10*      (2018.01)
*C07K 14/415*    (2006.01)

(52) U.S. Cl.
CPC ........... *C12N 15/8247* (2013.01); *A01H 5/10* (2013.01); *C07K 14/415* (2013.01)

(58) Field of Classification Search
None
See application file for complete search history.

(56) References Cited

U.S. PATENT DOCUMENTS 5,962,767 A * 10/1999 Ohlrogge ........... C12N 15/8247
                                                       435/419

OTHER PUBLICATIONS

Pyc et al, The Plant Journal, 2017, vol. 92, pp. 1182-1201. (Year: 2017).*
*Arabidopsis* Biological Resource Centre—mutant *Arabidopsis* line SALK_084555, Aug. 9, 2002. (Year: 2002).*
*Arabidopsis* Biological Resource Centre—mutant *Arabidopsis* line SAIL_335_H11, Jun. 28, 2004. (Year: 2004).*

* cited by examiner

*Primary Examiner* — Eileen B O Hara
(74) *Attorney, Agent, or Firm* — Jackson Walker LLP

(57) ABSTRACT

The present disclosure relates to increasing oil content in plants through manipulating expression of proteins, namely At5g16550 proteins. At5g16550 proteins are lipid droplet proteins. Plants having reduced expression of At5g16550 proteins demonstrate cytoplasmic lipid droplets (LDs) that are increased in size, resulting in greater overall oil content in the plant cells.

6 Claims, 14 Drawing Sheets
Specification includes a Sequence Listing.

FIG. 1B

```
AAAGCCACGTCGGTGCTACACATGTCCCTGATTTCTCCTTTAACATAAAACTAAACAGCTGTTTTGTCCGCAATCATT
ATCTATTACTAATAAAAAATCTCAACTTTTGTTCCTTACTCTTATTACTTCCTAAATCCGATCGAAACAACTGTTGGG
TTAGTTTCTAATTTCCAAGAATGGCGCAAGATCACGACGAGACGGAGAATAAAACCTTTGCCGACGTTGTCGGTGGCG
ATGATGTCGGCGAAATTGTCAACGGAGGAACAAAGAATGGCTATCGTAAACCGGACTCTGTGGAGAAGGAAGATGATG
AGGATTTGAAGAGTCTCTATTCCTTGATTTGTCTCACGATCGGTTCGATTCTGTTTCCAGATTCGAAAACCGGTGATG
CGTCTTCGTTTCTTGAACGTGTAAGAAACTCCGTCGCTGAAAATGGGCCTAAGCTTCGAGAAGCTTCTGAAAGAACAG
GACGCGAGATTCTTCTCTGGACTCGTAGAGGCAGCTCGCTTCGTGCTCTGCTTGTCATCACTGTAAGTAGAATGATTG
AACCTAATTAGAGACTGAATTTCATTTTCAATCTAGCCTTCCATTATCTTCAATTCGATTTCCTCAAGTAAATTAACG
TATTGTGCCCTAAATCGTCTTGGTTCTGTAACTCTTTACCATTGATGAAAAGTTTGGTACTTTATTGAAAAGTTTAGT
GCTTTATTGAACCCATTTGAGCCAAATTTCGTGGGTGTCTGAGACTATATGTTGATTAGTTATTATCTTGTTATTGTT
GTTGCAGATGGGAACAATAGTTCTTTTGACAACAATGGCTTTGGTTGTATTCACACTCTTCTTTGTAGCTGCAACAGC
CAATGCTATCATAATCTCTCTTCTGATTTCACTTGCTGTTGCTGGTGGCTTCTTGGCACTCTTCTTTCTCTGCTTGAC
TGGTGTTTACATTGGAGCCTTATCCGTTGCTGCATTCGTCATCTCTACCGCTACAGTTTCTGCTGTCGTTTCTGTCTT
AATAGCTTCAGGTTGGTTATATACTCTGCTCTGATTCTGTTTTGGAATCTTGTAATGAGTGACACTCCAAGTTACTTC
CTATATGTATTGAAGAATGAAATGAATTTGGTATTGGATCAGGTTGGATTGGGTTTTTCTATGCGGTGTGGTTGGGAA
CAAGAGGAAGCCTACGCTTGGCTAAGCAATCGGTTTCAGTGGTGGGATCAGCCATTTCAGGTAACACTATCAGTCGTC
ATCAACACCAAGACCGGGAGGTAAACATCGAATCAACCAACTGAGAATCCGTCCTTACCGCGTTTGTAAATAAACCCC
GACTTTTGGTTGTTAATGGAAGCTTGATATAAATATGATCTATGGAGTTTGTTGTGAAGAAGCAGAGAAAGAATGATA
AGAATATTTCAAAATGCAACTTGAAACATTTTGTGATCAATGTCTACGGATTTTTGGATCTATGTATGCATACATTGT
GTGTTTTATGTACTTAAGAAAGAATAATGATCAGTATCCATATGAAATCTCAACTC
(SEQ ID NO:2)
```

FIG. 12

```
Arabidopsis   MAQDHD----ETENKTPADVVGGD--DVGEIVNGGTKNGY-RKPDSVEKE-DDEDLKSLYS
Camelina      MAQDHDD---ETENKTYAGVVGGD--DVGEIVNGGTKNGYHRKPDFVEKEKDDEDLKSLYS
Rapeseed      MSQDHD----ETENKSYADAVGGDGDDAGETVKGETTNGD-RKTDSVKVD-EEDGSESLYS
Soybean       MAET------SNGNGVYVDEEEQE--------VVKLKQKTQR-------------VK--ETLPE
Peanut        MAEDKHSTNSNANGVYVEVTGEE--------ESNNNKRESE---------------SS--ITLYQ
Palm          MAETDEGS-KGTNGVSRVYIPRP--------IEIDGSGGGG---------------GG--ETLYA
Sunflower     MAVMN-----GGAEKPHGGVLSPEKETAETVENSTSKPDE---------KISTELGDDVTLYG
              *:                                                          :*

Arabidopsis   LICLTIGSILFPDSKTG--DASS---FLERVRNSVAENGPKLREASERTGREILLWTRRGS
Camelina      LVCLTIGSILFPDSKTGGGDASSSSFLERLKNSVAENGPKLREASARTGREILLWTRKGS
Rapeseed      LVCITIGSILFPDSKTG--YASSSPLLQRIRNSPAENGPKLREASKKTSREILQWTRRGS
Soybean       VLNRIASAILFPEPAYS---GS---LLRRIKLSVADHAPLLPEASKNSARDVLLWTRRGT
Peanut        VLNRLAYAILFPDPSTS----AS----LLKRIKISLAENAPLLPEASRKSALDLLLWTRQGS
Palm          VLRAFIAGVVSPDATAS----PPP-PLIQRLKASSAKAAPRFRQAFRNSAHDLLLWTRQGS
Sunflower     VSVHLIESILNQNSGSP---------MASRIKKSFVEAVPMFRKATVNTRREVVQWTR-GS
              :    :::  :.           :  *:: * ..  .: :*  .:  ::: *** *:

Arabidopsis   SLRALLVITMGTIVLLTTMALVVFTLFPVAATANAIIISLLISLAVAGGFLALFFLCLTG
Camelina      SLRALLVITVGTIVLLTTMALVVFTLFPVAATANAIIISLLISLAVAGGFLALFFLCLTG
Rapeseed      YLRALLVITMGTIGLVTMALVFALFPVAATFNAIIISLLVSLAAAGGFLALFFLSLAG
Soybean       PFRPLFVISVGTVTFVALTALLVFMLFFLAATINAIVISLLISLAAAGGFLALFAFVTA
Peanut        PFRAILVITVGTITSVALTGLLVFLLFFLAATINAVVISLLVSLAAAGGFLAIFFACVAA
Palm          PFRALLVISVGTITLLALTGLLVFMLFFLAATLNAIIAFLMSLAAAGGFLALFFACLTA
Sunflower     PIRALLVVSAGIVTLLALTGMLVFTVVFLAATVNAIVISLLISLAAVGGFLAIFFACMTP
              :*.::*::  *  :: ..::** :.:*** **:*:;*;***..*****;**  ::

Arabidopsis   VYIGALSVAAFVISTATVSAVVSVLIASGWIGFFYAVWLGTRGSLRLAKQSVSVVGSAIS
Camelina      VYIGALSIAAFVISTATVSAVVSVLIASGWIGFFYTVWLGTRGSLRLAKQSVSVVGSAIS
Rapeseed      IYIGALSVAAFVVSTVTISAVVSVLFASGWIGFFYAVWLGARGSLGLVKQSLSVMG----
Soybean       IYIGALAIAIFAISVTTFWSIVAILIITGFIGFIYTVWLVTRKSFPGFAKHSLDVTGSAIS
Peanut        VYVGALLVAAFAISVTTFWASVAVLFATGWIGFFYIVWLVTSKSFGYAKHTLSATGSAIS
Palm          IYIGALSVAVFIISTTTISTMIAVMIATGWVGFFCVVWLAVKKSVNLTKQSLSMTSSAIS
Sunflower     MYIGLLFVTAFVTFTVTISSIIAALVAAGWIGFIWMIWLAASEGARMVKRVTYAAN--AS
              :*:*  *  ::  *   ..*. :.:: :. :*:****:  :**  .  .   .:    .

Arabidopsis   GNTISRHQHQDREVNIESTN
Camelina      GNSASRHQHQDREVNIESSN
Rapeseed      GNTFSRHQHKYREVNIESSS
Soybean       SYTTARHAH--HLIHTNSK-
Peanut        TYSAARHVR--EQMRKDSD-
Palm          AYSAARHAR--HYVSSKSAD
Sunflower     GQLNPRTF------------
                     *
```

US 10,308,950 B2

SEQUENCE LISTING

```
<160> NUMBER OF SEQ ID NOS: 8

<210> SEQ ID NO 1
<211> LENGTH: 249
<212> TYPE: PRT
<213> ORGANISM: Arabidopsis thaliana

<400> SEQUENCE: 1

Met Ala Gln Asp His Asp Glu Thr Glu Asn Lys Thr Phe Ala Asp Val
1               5                   10                  15

Val Gly Gly Asp Asp Val Gly Glu Ile Val Asn Gly Gly Thr Lys Asn
            20                  25                  30

Gly Tyr Arg Lys Pro Asp Ser Val Glu Lys Glu Asp Asp Glu Asp Leu
        35                  40                  45

Lys Ser Leu Tyr Ser Leu Ile Cys Leu Thr Ile Gly Ser Ile Leu Phe
    50                  55                  60
```

Pro Asp Ser Lys Thr Gly Asp Ala Ser Ser Phe Leu Glu Arg Val Arg
65              70                  75                  80

Asn Ser Val Ala Glu Asn Gly Pro Lys Leu Arg Glu Ala Ser Glu Arg
            85                  90                  95

Thr Gly Arg Glu Ile Leu Leu Trp Thr Arg Arg Gly Ser Ser Leu Arg
        100                 105                 110

Ala Leu Leu Val Ile Thr Met Gly Thr Ile Val Leu Thr Thr Met
        115                 120                 125

Ala Leu Val Val Phe Thr Leu Phe Phe Val Ala Ala Thr Ala Asn Ala
        130                 135                 140

Ile Ile Ile Ser Leu Leu Ile Ser Leu Ala Val Ala Gly Gly Phe Leu
145                 150                 155                 160

Ala Leu Phe Phe Leu Cys Leu Thr Gly Val Tyr Ile Gly Ala Leu Ser
                165                 170                 175

Val Ala Ala Phe Val Ile Ser Thr Ala Thr Val Ser Ala Val Val Ser
            180                 185                 190

Val Leu Ile Ala Ser Gly Trp Ile Gly Phe Phe Tyr Ala Val Trp Leu
        195                 200                 205

Gly Thr Arg Gly Ser Leu Arg Leu Ala Lys Gln Ser Val Ser Val Val
210                 215                 220

Gly Ser Ala Ile Ser Gly Asn Thr Ile Ser Arg His Gln His Gln Asp
225                 230                 235                 240

Arg Glu Val Asn Ile Glu Ser Thr Asn
            245

<210> SEQ ID NO 2
<211> LENGTH: 1538
<212> TYPE: DNA
<213> ORGANISM: Arabidopsis thaliana

<400> SEQUENCE: 2

```
aaagccacgt cggtgctaca catgtccctg atttctcctt taacataaaa ctaaacagct      60
gttttgtccg caatcattat ctattactaa taaaaaatct caacttttgt tccttactct     120
tattacttcc taaatccgat cgaaacaact gttgggttag tttctaattt ccaagaatgg     180
cgcaagatca cgacgagacg gagaataaaa cctttgccga cgttgtcggt ggcgatgatg     240
tcggcgaaat tgtcaacgga ggaacaaaga tggctatcg taaaccggac tctgtggaga     300
aggaagatga tgaggatttg aagagtctct attccttgat ttgtctcacg atcggttcga     360
ttctgtttcc agattcgaaa accggtgatg cgtcttcgtt tcttgaacgt gtaagaaact     420
ccgtcgctga aaatgggcct aagcttcgag aagcttctga agaacagga cgcgagattc     480
ttctctggac tcgtagaggc agctcgcttc gtgtctctgct tgtcatcact gtaagtagaa     540
tgattgaacc taattagaga ctgaatttca ttttcaatct agccttccat tatcttcaat     600
tcgatttcct caagtaaatt aacgtattgt gccctaaatc gtcttggttc tgtaactctt     660
taccattgat gaaaagtttg gtactttatt gaaaagttta gtgctttatt gaacccattt     720
gagccaaatt tcgtgggtgt ctgagactat atgttgatta gttattatct tgttattgtt     780
gttgcagatg ggaacaatag ttcttttgac aacaatggct tggttgtat tcacactctt     840
ctttgtagct gcaacagcca atgctatcat aatctctctt ctgatttcac ttgctgttgc     900
tggtggcttc ttggcactct tctttctctg cttgactggt gtttacattg gagccttatc     960
cgttgctgca ttcgtcatct ctaccgctac agttctgct gtcgtttctg tcttaatagc    1020
ttcaggttgg ttatatactc tgctctgatt ctgttttgga atcttgtaat gagtgacact    1080
```

-continued

```
ccaagttact tcctatatgt attgaagaat gaaatgaatt tggtattgga tcaggttgga    1140
ttgggttttt ctatgcggtg tggttgggaa caagaggaag cctacgcttg gctaagcaat    1200
cggtttcagt ggtgggatca gccatttcag gtaacactat cagtcgtcat caacaccaag    1260
accgggaggt aaacatcgaa tcaaccaact gagaatccgt ccttaccgcg tttgtaaata    1320
aaccccgact tttggttgtt aatggaagct tgatataaat atgatctatg gagtttgttg    1380
tgaagaagca gagaaagaat gataagaata tttcaaaatg caacttgaaa cattttgtga    1440
tcaatgtcta cggattttg gatctatgta tgcatacatt gtgtgtttta tgtacttaag    1500
aaagaataat gatcagtatc catatgaaat ctcaactc                            1538
```

<210> SEQ ID NO 3
<211> LENGTH: 233
<212> TYPE: PRT
<213> ORGANISM: Elaeis guineensis

<400> SEQUENCE: 3

```
Met Ala Glu Thr Asp Glu Gly Ser Lys Gly Thr Asn Gly Val Ser Arg
1               5                   10                  15

Val Tyr Ile Pro Arg Pro Ile Glu Ile Asp Gly Ser Gly Gly Gly Gly
            20                  25                  30

Gly Gly Glu Thr Leu Tyr Ala Val Leu Arg Ala Phe Ile Ala Gly Val
        35                  40                  45

Val Ser Pro Asp Ala Thr Ala Ser Pro Pro Pro Leu Ile Gln Arg
    50                  55                  60

Leu Lys Ala Ser Ser Ala Lys Ala Pro Arg Phe Arg Gln Ala Phe
65                  70                  75                  80

Arg Asn Ser Ala His Asp Leu Leu Leu Trp Thr Arg Gln Gly Ser Pro
                85                  90                  95

Phe Arg Ala Leu Leu Val Ile Ser Val Gly Thr Ile Thr Leu Leu Ala
            100                 105                 110

Leu Thr Gly Leu Leu Val Phe Met Leu Phe Phe Leu Ala Ala Thr Leu
        115                 120                 125

Asn Ala Ile Ile Ile Ala Phe Leu Met Ser Leu Ala Ala Gly Gly
    130                 135                 140

Phe Leu Ala Leu Phe Phe Ala Cys Leu Thr Ala Ile Tyr Ile Gly Ala
145                 150                 155                 160

Leu Ser Val Ala Val Phe Ile Ile Ser Thr Thr Thr Ile Ser Thr Met
                165                 170                 175

Ile Ala Val Met Ile Ala Thr Gly Trp Val Gly Phe Phe Cys Val Val
            180                 185                 190

Trp Leu Ala Val Lys Lys Ser Val Asn Leu Thr Lys Gln Ser Leu Ser
        195                 200                 205

Met Thr Ser Ser Ala Ile Ser Ala Tyr Ser Ala Ala Arg His Ala Arg
    210                 215                 220

His Tyr Val Ser Ser Lys Ser Ala Asp
225                 230
```

<210> SEQ ID NO 4
<211> LENGTH: 226
<212> TYPE: PRT
<213> ORGANISM: Glycine max

<400> SEQUENCE: 4

Met Ala Glu Thr Ser Asn Gly Asn Gly Val Tyr Val Asp Glu Glu Glu

```
                1               5                      10                      15
            Gln Glu Val Val Lys Leu Lys Gln Lys Thr Gln Arg Val Lys Glu Thr
                            20                      25                      30

Leu Pro Glu Val Leu Asn Arg Ile Ala Ser Ala Ile Leu Phe Pro Glu
                            35                      40                      45

Pro Ala Tyr Ser Gly Ser Leu Leu Arg Arg Ile Lys Leu Ser Val Ala
                            50                      55                      60

Asp His Ala Pro Leu Leu Pro Glu Ala Ser Lys Asn Ser Ala Arg Asp
            65                      70                      75                      80

Val Leu Leu Trp Thr Arg Arg Gly Thr Pro Phe Arg Pro Leu Phe Val
                            85                      90                      95

Ile Ser Val Gly Thr Val Thr Phe Val Ala Leu Thr Ala Leu Leu Val
                            100                     105                     110

Phe Met Leu Phe Leu Ala Ala Thr Ile Asn Ala Ile Val Ile Ser
                            115                     120                     125

Leu Leu Ile Ser Leu Ala Ala Ala Gly Gly Phe Leu Ala Leu Phe Phe
                            130                     135                     140

Ala Phe Val Thr Ala Ile Tyr Ile Gly Ala Leu Ala Ile Ala Ile Phe
            145                     150                     155                     160

Ala Ile Ser Val Thr Thr Phe Trp Ser Ile Val Ala Ile Leu Ile Ile
                            165                     170                     175

Thr Gly Phe Ile Gly Phe Ile Tyr Thr Val Trp Leu Val Thr Arg Lys
                            180                     185                     190

Ser Phe Gly Phe Ala Lys His Ser Leu Asp Val Thr Gly Ser Ala Ile
                            195                     200                     205

Ser Ser Tyr Thr Thr Ala Arg His Ala His His Leu Ile His Thr Asn
                            210                     215                     220

Ser Lys
            225

<210> SEQ ID NO 5
            <211> LENGTH: 249
            <212> TYPE: PRT
            <213> ORGANISM: Brassica napus

<400> SEQUENCE: 5

Met Ser Gln Asp His Asp Glu Thr Glu Asn Lys Ser Tyr Ala Asp Ala
            1                       5                       10                      15

Val Gly Gly Asp Gly Asp Ala Gly Glu Thr Val Lys Gly Glu Thr
                            20                      25                      30

Thr Asn Gly Asp Arg Lys Thr Asp Ser Val Lys Val Asp Glu Glu Asp
                            35                      40                      45

Gly Ser Glu Ser Leu Tyr Ser Leu Val Cys Ile Thr Ile Gly Ser Ile
                            50                      55                      60

Leu Phe Pro Asp Ser Lys Thr Gly Tyr Ala Ser Ser Ser Pro Leu Leu
            65                      70                      75                      80

Gln Arg Ile Arg Asn Ser Phe Ala Glu Asn Gly Pro Lys Leu Arg Glu
                            85                      90                      95

Ala Ser Lys Lys Thr Ser Arg Glu Ile Leu Gln Trp Thr Arg Arg Gly
                            100                     105                     110

Ser Tyr Leu Arg Ala Leu Leu Val Ile Thr Met Gly Thr Ile Gly Leu
                            115                     120                     125

Val Thr Thr Met Ala Leu Val Val Phe Ala Leu Phe Phe Val Ala Ala
                            130                     135                     140
```

```
Thr Phe Asn Ala Ile Ile Ile Ser Leu Leu Val Ser Leu Ala Ala Ala
145                 150                 155                 160

Gly Gly Phe Leu Ala Leu Phe Phe Leu Ser Leu Ala Gly Ile Tyr Ile
                165                 170                 175

Gly Ala Leu Ser Val Ala Ala Phe Val Val Ser Thr Val Thr Ile Ser
                180                 185                 190

Ala Val Val Ser Val Leu Phe Ala Ser Gly Trp Ile Gly Phe Phe Tyr
            195                 200                 205

Ala Val Trp Leu Gly Ala Arg Gly Ser Leu Gly Leu Val Lys Gln Ser
            210                 215                 220

Leu Ser Val Met Gly Gly Asn Thr Phe Ser Arg His Gln His Lys Tyr
225                 230                 235                 240

Arg Glu Val Asn Ile Glu Ser Ser Ser
                245

<210> SEQ ID NO 6
<211> LENGTH: 256
<212> TYPE: PRT
<213> ORGANISM: Camelina sativa

<400> SEQUENCE: 6

Met Ala Gln Asp His Asp Asp Glu Thr Glu Asn Lys Thr Tyr Ala Gly
1               5                   10                  15

Val Val Gly Gly Asp Asp Val Gly Glu Ile Val Asn Gly Gly Thr Lys
                20                  25                  30

Asn Gly Tyr His Arg Lys Pro Asp Phe Val Glu Lys Glu Lys Asp Asp
                35                  40                  45

Glu Asp Leu Lys Ser Leu Tyr Ser Leu Val Cys Leu Thr Ile Gly Ser
50                  55                  60

Ile Leu Phe Pro Asp Ser Lys Thr Gly Gly Asp Ala Ser Ser Ser
65                  70                  75                  80

Ser Phe Leu Glu Arg Leu Lys Asn Ser Val Ala Glu Asn Gly Pro Lys
                85                  90                  95

Leu Arg Glu Ala Ser Ala Arg Thr Gly Arg Glu Ile Leu Leu Trp Thr
                100                 105                 110

Arg Lys Gly Ser Ser Leu Arg Ala Leu Leu Val Ile Thr Val Gly Thr
            115                 120                 125

Ile Val Leu Leu Thr Thr Met Ala Leu Val Val Phe Thr Leu Phe Phe
130                 135                 140

Val Ala Ala Thr Ala Asn Ala Ile Ile Ile Ser Leu Leu Ile Ser Leu
145                 150                 155                 160

Ala Val Ala Gly Gly Phe Leu Ala Leu Phe Phe Leu Cys Leu Thr Gly
                165                 170                 175

Val Tyr Ile Gly Ala Leu Ser Ile Ala Ala Phe Val Ile Ser Thr Ala
                180                 185                 190

Thr Val Ser Ala Val Val Ser Val Leu Ile Ala Ser Gly Trp Ile Gly
            195                 200                 205

Phe Phe Tyr Thr Val Trp Leu Gly Thr Arg Gly Ser Leu Arg Leu Ala
            210                 215                 220

Lys Gln Ser Val Ser Val Val Gly Ser Ala Ile Ser Gly Asn Ser Ala
225                 230                 235                 240

Ser Arg His Gln His Gln Asp Arg Glu Val Asn Ile Glu Ser Ser Asn
                245                 250                 255

<210> SEQ ID NO 7
```

-continued

```
<211> LENGTH: 226
<212> TYPE: PRT
<213> ORGANISM: Helianthus annuus

<400> SEQUENCE: 7

Met Ala Val Met Asn Gly Gly Ala Glu Lys Pro His Gly Gly Val Leu
1               5                   10                  15

Ser Pro Glu Lys Glu Thr Ala Glu Thr Val Glu Asn Ser Thr Ser Lys
            20                  25                  30

Pro Asp Glu Asp Ile Ser Thr Glu Leu Gly Asp Asp Val Thr Leu Tyr
        35                  40                  45

Gly Val Ser Val His Leu Ile Glu Ser Ile Leu Asn Gln Asn Ser Gly
    50                  55                  60

Ser Pro Met Ala Ser Arg Ile Lys Lys Ser Phe Val Glu Ala Val Pro
65                  70                  75                  80

Met Phe Arg Lys Ala Thr Val Asn Thr Arg Arg Glu Val Val Gln Trp
                85                  90                  95

Thr Arg Gly Ser Pro Ile Arg Ala Leu Leu Val Val Ser Ala Gly Ile
            100                 105                 110

Val Thr Leu Leu Ala Leu Thr Gly Met Leu Val Phe Thr Val Phe
        115                 120                 125

Leu Ala Ala Thr Val Asn Ala Ile Val Ile Ser Leu Leu Ile Ser Leu
    130                 135                 140

Ala Ala Val Gly Gly Phe Leu Ala Ile Phe Phe Ala Cys Met Thr Thr
145                 150                 155                 160

Met Tyr Ile Gly Leu Leu Phe Val Thr Ala Phe Val Thr Phe Thr Val
                165                 170                 175

Thr Ile Ser Ser Ile Ile Ala Ala Leu Val Ala Ala Gly Trp Ile Gly
            180                 185                 190

Phe Ile Trp Met Ile Trp Leu Ala Ala Ser Glu Gly Ala Arg Met Val
        195                 200                 205

Lys Arg Val Thr Tyr Ala Ala Asn Ala Ser Gly Gln Leu Asn Pro Arg
    210                 215                 220

Thr Phe
225

<210> SEQ ID NO 8
<211> LENGTH: 231
<212> TYPE: PRT
<213> ORGANISM: Arachis hypogaea

<400> SEQUENCE: 8

Met Ala Glu Asp Lys His Ser Thr Asn Ser Asn Ala Asn Gly Val Tyr
1               5                   10                  15

Val Glu Val Thr Gly Glu Glu Ser Asn Asn Asn Lys Arg Glu Ser
            20                  25                  30

Glu Ser Ser Ile Thr Leu Tyr Gln Val Leu Asn Arg Leu Ala Tyr Ala
        35                  40                  45

Ile Leu Phe Pro Asp Pro Ser Thr Ser Ala Ser Leu Leu Lys Arg Ile
    50                  55                  60

Lys Ile Ser Leu Ala Glu Asn Ala Pro Leu Leu Pro Glu Ala Ser Arg
65                  70                  75                  80

Lys Ser Ala Leu Asp Leu Leu Leu Trp Thr Arg Gln Gly Ser Pro Phe
                85                  90                  95

Arg Ala Ile Leu Val Ile Thr Val Gly Thr Ile Thr Ser Val Ala Leu
            100                 105                 110
```

-continued

```
Thr Gly Leu Leu Val Phe Leu Leu Phe Phe Leu Ala Ala Thr Ile Asn
        115                 120                 125

Ala Val Val Ile Ser Leu Leu Val Ser Leu Ala Ala Ala Gly Gly Phe
        130                 135                 140

Leu Ala Ile Phe Phe Ala Cys Val Ala Ala Val Tyr Val Gly Ala Leu
145                     150                 155                 160

Leu Val Ala Ala Phe Ala Ile Ser Val Thr Thr Phe Trp Ala Ser Val
                165                 170                 175

Ala Val Leu Phe Ala Thr Gly Trp Ile Gly Phe Phe Tyr Ile Val Trp
                180                 185                 190

Leu Val Thr Ser Lys Ser Phe Gly Tyr Ala Lys His Thr Leu Ser Ala
        195                 200                 205

Thr Gly Ser Ala Ile Ser Thr Tyr Ser Ala Ala Arg Lys Val Arg His
        210                 215                 220

Trp Met Arg Lys Asp Ser Asp
225                 230
```

METHODS FOR INCREASING OIL CONTENT IN PLANT TISSUES BY SUPPRESSING HYDROPHOBIC LIPID DROPLET PROTEIN

This application claims priority to U.S. Provisional Patent Application Ser. No. 62/350,843, entitled "Methods for Increasing Oil content in Plant Tissues by Suppressing Hydrophobic Lipid Droplet Protein," filed on Jun. 16, 2016, the entire contents of which are hereby incorporated by reference.

BACKGROUND

This disclosure pertains to regulation of oil content in plant tissues through manipulation of proteins.

Cytoplasmic lipid droplets (LDs) are evolutionarily conserved organelles found in a wide range of unicellular and multicellular organisms. Uniquely delineated by a single phospholipid monolayer and coated with a diverse set of proteins, LDs function primarily in the storage of energy-rich neutral lipids, such as triacylglycerols. In plants, LDs have been studied mostly in oilseeds, although all plant cell types, including vegetative tissues, have the machinery required for accumulating and storing lipids in LDs.

A number of high value oils are produced by plants, and increasing the oil content in the cells of these oil-producing plants would be highly advantageous to the supply of these oils.

SUMMARY

The present disclosure relates generally to increasing oil content in plant cells. In particular, this disclosure pertains to manipulation of proteins in order to affect regulation of cytoplasmic lipid droplets (LDs) in plant cells.

A class of proteins in *Arabidopsis thaliana* (*Arabidopsis*) has been identified and named LD-associated proteins (LDAPs). These proteins are abundant components of LDs in non-seed cell types and are required for their proper compartmentation. In an effort to identify other novel LD proteins, the LDAPs were used as 'bait' proteins in yeast two-hybrid screens against an *Arabidopsis* cDNA 'prey' library. One LDAP3 interactor, encoded by gene At5g16550 (based on the genome sequence annotation for *Arabidopsis* at TAIR [The *Arabidopsis* Information Resource]), is a protein annotated to be of unknown function, but possesses a unique mycobacterial membrane protein large (MMPL) domain found in members of the *M. tuberculosis* protein family involved in lipid transport. Similar to the LDAPs, At5g16550 is expressed in *Arabidopsis* in a variety of tissues and at various developmental stages, and is targeted to the LD surface with high specificity in leaf cells. Furthermore, analyses of an *Arabidopsis* at5g16550 mutant revealed conspicuously enlarged LDs and increased neutral lipid content in both leaves and mature seeds, demonstrating that At5g16550 plays a role in regulating LD size and neutral lipid levels in plant cells.

The present disclosure relates generally to reduction or elimination of gene expression of At5g16550 or its homolog in plants in order to increase oil content. Preferred embodiments include transgenic plants or seeds having suppressed gene expression of AT5G16550 or its homologs and which produce increased oil content through the inclusion of substantially larger LDs.

BRIEF DESCRIPTION OF THE DRAWINGS

FIG. 1B. shows the genomic sequence of the *Arabidopsis* At5g16550 gene, with sequences corresponding to the three exons in the At5g16550 gene in bold type and 5' and 3' untranslated regions (UTRs) italicized (SEQ ID NO:2).

Figure 10A:
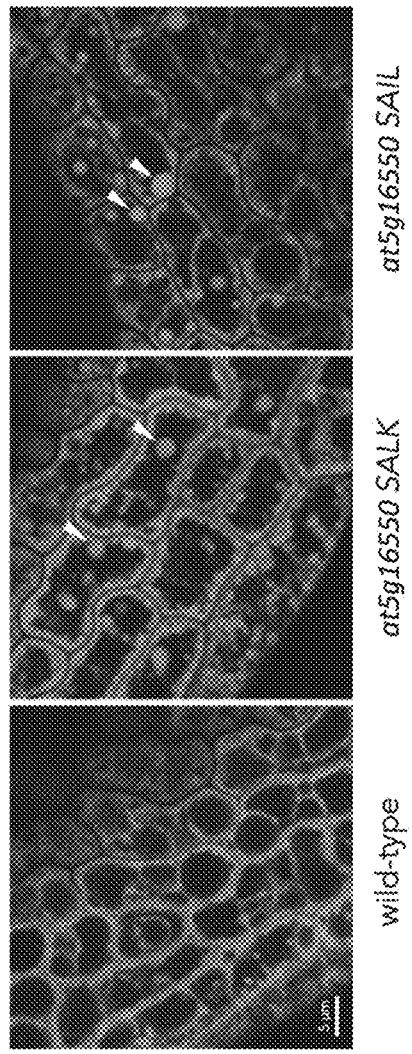
FIG. 10A shows CLSM images of BODIPY-stained LDs in wild-type (WT), and at5g16550 SAIL_335_H11 (knockout) and SALK_084555 (knockdown) mature, dry *Arabi-* dopsis seeds, with arrowheads highlighting examples of enlarged LDs in both knockdown and knockout mutant seeds.
Figure 10B:
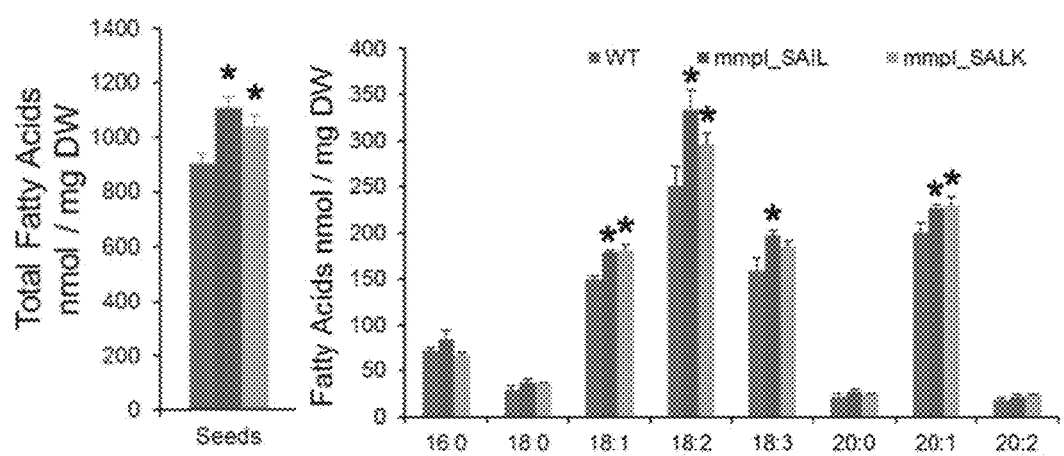

FIG. 10B shows total fatty acid content (left) and content of different fatty acids (right) in WT and at5g16550 SAIL_335_H11 (knockout) and SALK_084555 (knockdown) mature, dry Arabidopsis seeds.

Figure 11A:
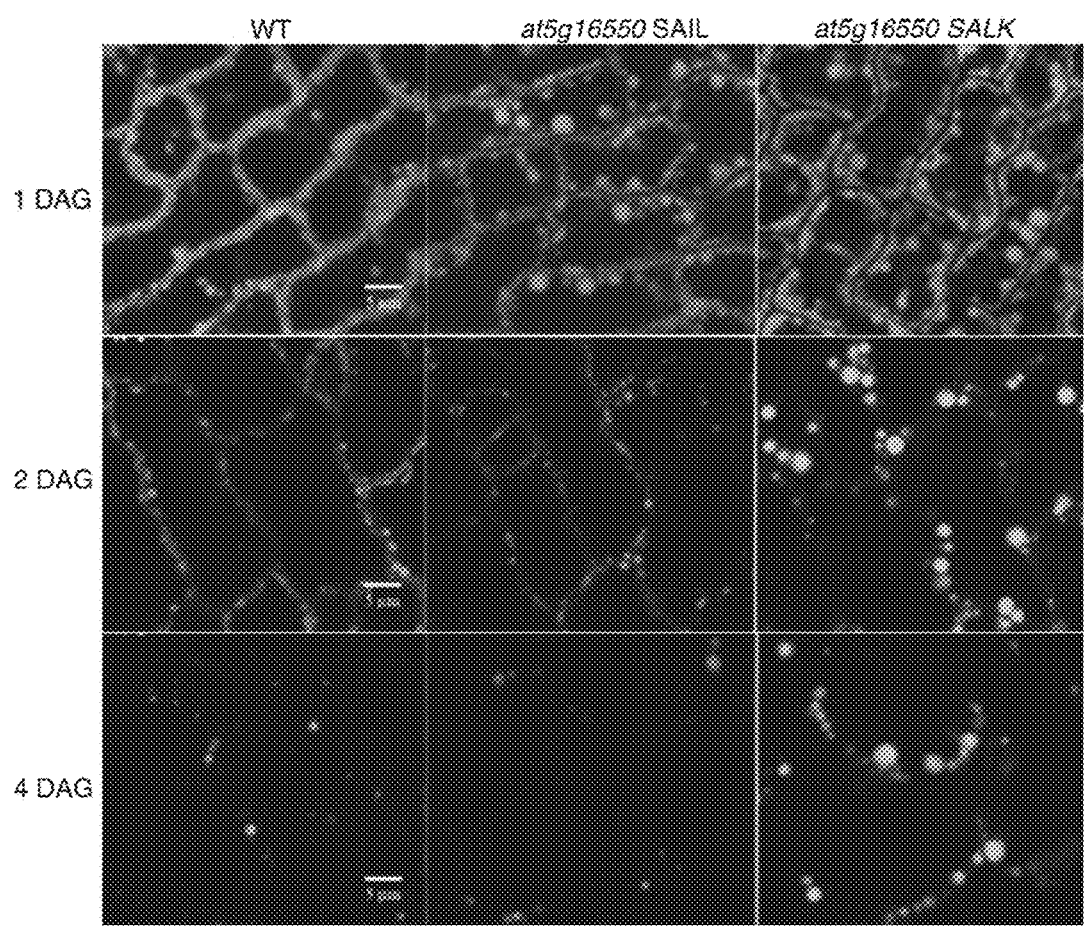

FIG. 11A shows CLSM images of BODIPY-stained LDs in WT and at5g16550 SAIL_335_H11 (knockout) and SALK_084555 (knockdown) Arabidopsis seedlings 1, 2 and 4 days after germination (DAG), shown in top, middle and bottom row of micrographs, respectively.

Figure 11B:
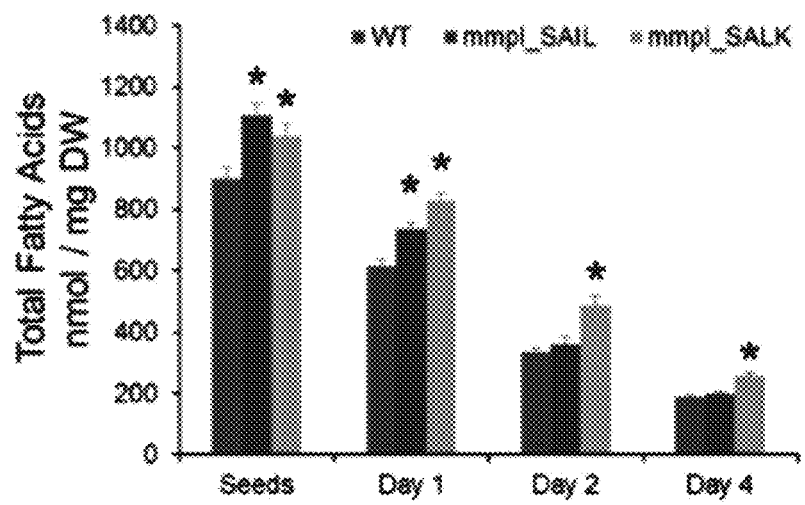

FIG. 11B shows total fatty acid content in WT and at5g16550 SAIL_335_H11 (knockout) and SALK_084555 (knockdown) Arabidopsis seedlings 1, 2 and 4 days after germination.

Figure 11C:
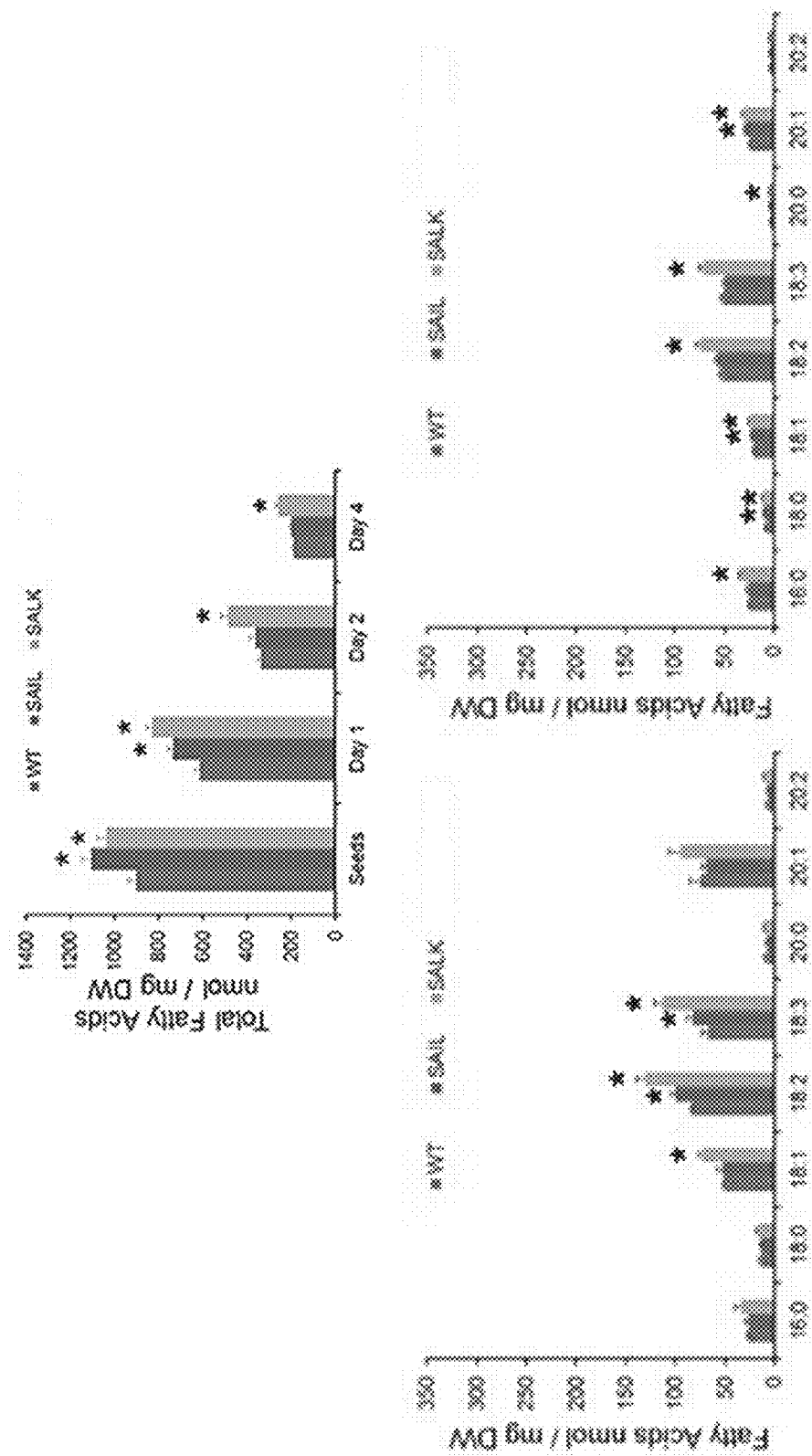

FIG. 11C shows content of different fatty acids in WT and at5g16550 SAIL_335_H11 (knockout) and SALK_084555 (knockdown) Arabidopsis seedlings 1, 2 and 4 days after germination, shown in top and bottom left and right graphs, respectively.

FIG. 12 shows a CLUSTALW amino acid alignment of Arabidopsis At5g16550 (SEQ ID NO:1) with potential orthologous proteins from major oilseed crops, including palm (Genbank accession XP_010905612.1) (SEQ ID NO:3), soybean (XP_003538382.1) (SEQ ID NO:4), rapeseed (XP_013649840.1) (SEQ ID NO:5), camelina (XP_010492567.1) (SEQ ID NO:6), sunflower (OTF96048.1) (SEQ ID NO:7), and peanut (PeanutBase accession Aradu.C5TRQ) (SEQ ID NO:8), with identical and similar amino acid residues indicated with asterisks and colons or periods, respectively.

DETAILED DESCRIPTION OF PREFERRED EMBODIMENTS

Generally, the present disclosure relates to increasing the occurrence and size of cytoplasmic lipid droplets (LDs) in seeds and leaves through reduction or elimination of expression of certain proteins, namely a protein encoded by gene At5g16550 in Arabidopsis thaliana, or its homolog in related plant species. Preferred embodiments include methods for producing plants having increased size of LDs or oil content by introducing mutations in At5g16550 protein-coding genes or their homologs to reduce or eliminate expression of these proteins. Additional preferred embodiments include plants, plant cells, or plant seeds having mutations in At5g16550 like proteins, which produce LDs with increased size or oil content in the resulting plants. Further, overexpression of At5g16550 or its homologs in plant cells will yield an increase in LD number.

The examples described herein are carried out with particular attention to Arabidopsis plants and the Arabidopsis protein encoded by gene At5G16550 (gene locus identifier based on the genome sequence annotation for Arabidopsis at TAIR). However, Arabidopsis is frequently used as a representative plant system (Koornneef and Meinke, 2010; Provart et al., 2016), including for oilseed crops (Wallis and Brown, 2010; Li-Beisson et al., 2013) and, accordingly, it is expected that similar results would be obtained for any plant through similar manipulation of homologs of At5g16550 proteins. Homologs of Arabidopsis of At5g16550 are broadly conserved in higher to lower plant species and the majority of plant species contain one or, in those plants whose genomes underwent whole-genome duplications, two At5g16550-like proteins.

EXAMPLE 1

Sequence and Hydropathy Profile

The deduced amino acid sequence of Arabidopsis At5g16550 is shown below:

```
                                                 (SEQ ID NO: 1)
MAQDHDETEN KTFADVVGGD DVGEIVNGGT KNGYRKPDSV EKEDDEDLKS  50

LYSLICLTIG SILFPDSKTG DASSFLERVR NSVAENGPKL REASERTGRE 100

ILLWTRRGSS LRALLVITMG TIVLLTTMAL VVFTLFFVAA TANAIIISLL 150

ISLAVAGGFL ALFFLCLTGV YIGALSVAAF VISTATVSAV VSVLIASGWI 200

GFFYAVWLGT RGSLRLAKQS VSVVGSAISG NTISRHQHQD REVNIESTN* 249
```

Figure 1A:
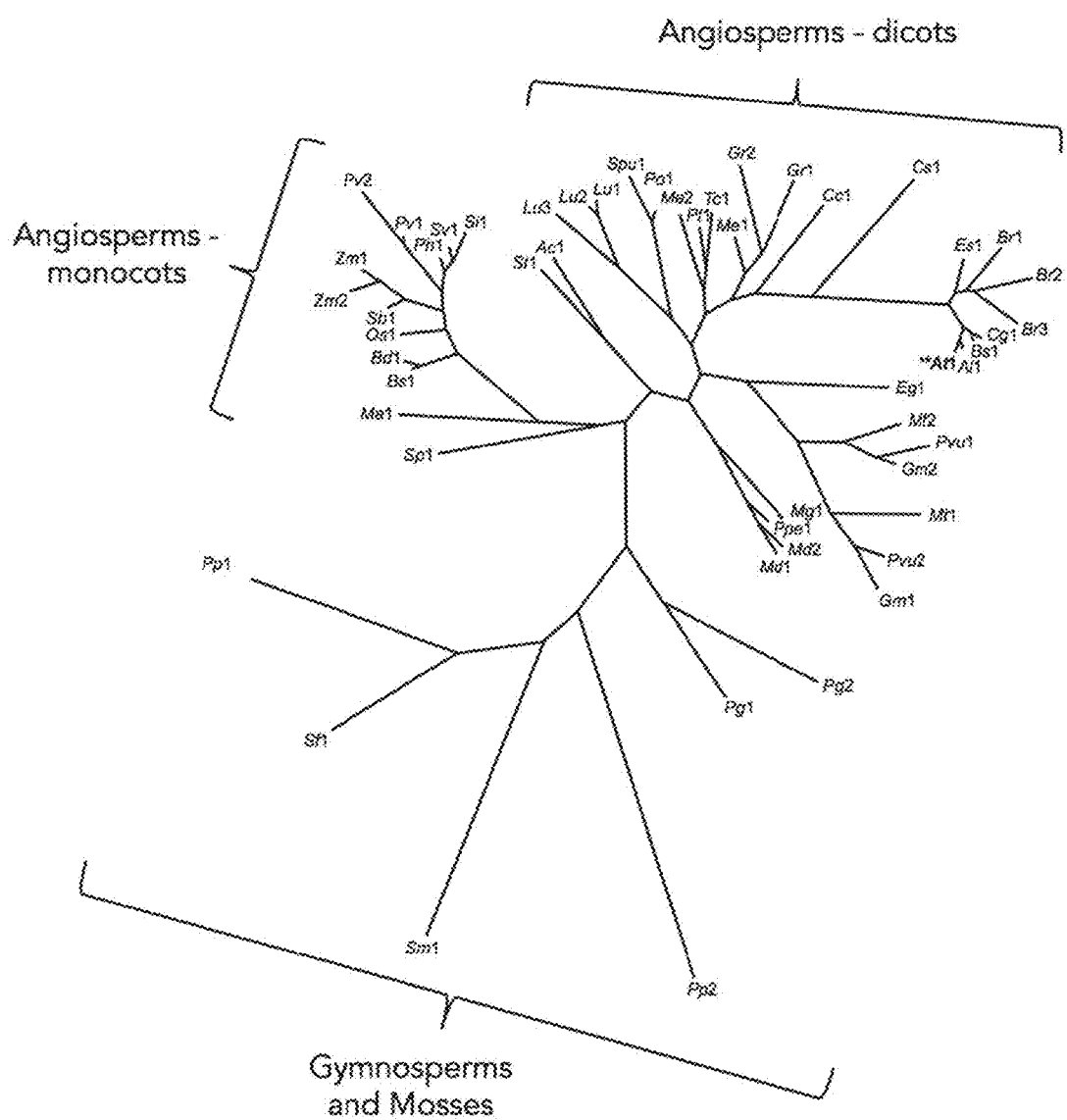
FIG. 1A shows a phylogenic tree of *Arabidopsis* At5g16550 (**At1) and its predicted protein homologs in plants, including other angiosperms (dicots and monocots), as well as gymnosperms and mosses, generated using TreeView with sequence alignment generated using BioEdit.

This protein was identified in a yeast two-hybrid screen of an Arabidopsis cDNA library using the Arabidopsis lipid droplet-associated protein isoform 3 (LDAP3) as 'bait.' At5g16550 is the only protein in Arabidopsis annotated (based on previous annotations at TAIR (The Arabidopsis Information Resource) and the National Centre for Biotechnology Information [NCBI; ncbi.nlm.nih.gov]) to contain an MMPL domain, a membrane transport protein domain. The N-terminal sequence upstream of the MMPL domain in Arabidopsis At5g16550 is found at residues 1-106, the C-terminal sequence downstream of the MMPL domain is found at residues 212-249, and the MMPL domain sequence is found at residues 107-211. MMPL domain-containing proteins are present also in the mycobacterial membrane protein large (MMPL) family of proteins in M. tuberculosis, wherein they serve as cell membrane proteins involved in transport of various lipids across the cell membrane to the cell wall (Tekaia et al., 1999; Pacheco et al., 2013; Viljoen et al., 2017 and references therein). Similar to the plant-specific LDAPs (Gidda et al., 2012; Horn et al., 2013; Divi et al., 2016), homologs of Arabidopsis At5g16550 are broadly conserved in all plant species, including mosses, gymnosperms, and angiosperms (with reference to the phylogenetic tree shown in FIG. 1A), and other than the abovementioned MMPL-domain-containing proteins in M. tuberculosis, they appear to be specific to the plant kingdom. Further, while many plant species contain only one copy of an At5g16550-like gene, others, such as grasses, Brassiceae and legumes, possess two copies, consistent with their past whole-genome duplications. FIG. 1B shows the full sequence of the At5g16550 gene (SEQ ID NO:2), based on TAIR (The Arabidopsis Information Resource). In FIG. 1A, sequences were obtained from Phytozome and abbreviations are based on the genus and species and gene copy number, e.g., in Arabidopsis thaliana (At1) At5g16550 is present as a single copy; two At5g16550-like genes exist in Glycine max (Gm1 and Gm2).

Figure 2:
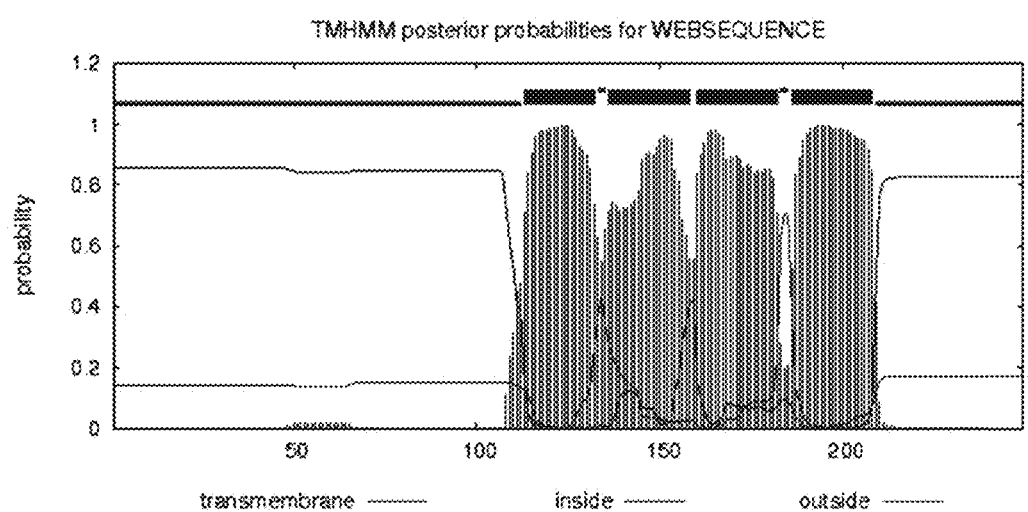
FIG. 2 shows a hydropathy profile of *Arabidopsis* At5g16550 (based on the Center of Biological Sequence Analysis [CBS; cbs.dtu.dk]).

FIG. 2 shows a hydropathy profile of *Arabidopsis* At5g16550 (based on the Center of Biological Sequence Analysis [CBS; cbs.dtu.dk]), which reveals an extensive hydrophobic region corresponding to the protein's MMPL domain-like sequence (residues 107-211). Without wanting to be bound by theory, based on the characterization of members of the *M. tuberculosis* MMPL family (Converse et al., 2003; Varela et al., 2012; Pacheco et al., 2013), the MMPL-domain-like sequence in the *Arabidopsis* At5g16550 protein may serve as a membrane anchor and/or a channel for transporting lipids.

EXAMPLE 2

Intracellular Localization, Expression, and Interaction with LDAP3

Figure 3A:
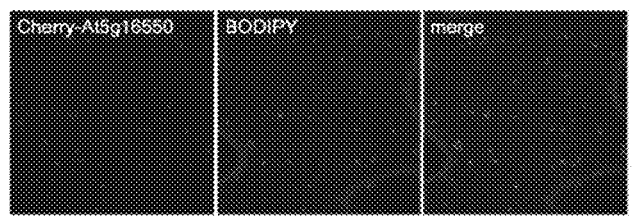
FIG. 3A shows confocal laser-scanning microscopy (CLSM) images of transiently-expressed Cherry-tagged full-length *Arabidopsis* At5g16550 localized to BODIPY 493/503-stained cytoplasmic lipid droplets (LDs) in a tobacco leaf cell, with the corresponding merged image.
Figure 3B:
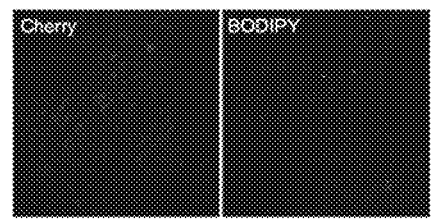
FIG. 3B shows CSLM images of transiently-expressed Cherry alone and BODIPY 493/503-stained cytoplasmic LDs in a tobacco leaf cell.

FIG. 3A shows representative confocal laser-scanning microscopy (CLSM) images of Cherry-tagged full-length *Arabidopsis* At5g16550 localized to cytoplasmic lipid droplets (LDs) in tobacco leaf epidermal (pavement) cells. Leaves of 4-week-old tobacco (*Nicotiana benthamiana*) plants were co-infiltrated with *Agrobacterium tumefaciens* carrying binary vectors encoding Cherry-At5g16550 (pMDC32/Cherry-At5g16550 driven by the 35S constitutive promoter) or the tomato bushy stunt virus P19 to enhance transgene expression according to the methods described elsewhere (McCartney et al., 2005; Petrie et al., 2010; Cai et al., 2015). LDs were stained with the fluorescent neutral lipid dye BODIPY 493/503. Microscopic images were acquired using a Leica DM RBE microscope with a Leica TCS SP2 scanning head, and the Leica TCS NT software package (Leica). Based on the merged image, Cherry-At5g16550 localizes to LDs in tobacco leaf cells, similar to the intracellular localization reported for its putative interacting protein partner, LDAP3 (Horn et al., 2012; Gidda et al., 2016). Further, compared to the CLSM images of BODIPY-stained LDs in tobacco leaf cells transiently expressing the Cherry fluorescent protein alone (FIG. 3B), ectopic expression of Cherry-At5g16550 appears to result in a relative increase in LD numbers in tobacco leaf cells (compare BODIPY staining in FIGS. 3A and 3B).

Figure 4:
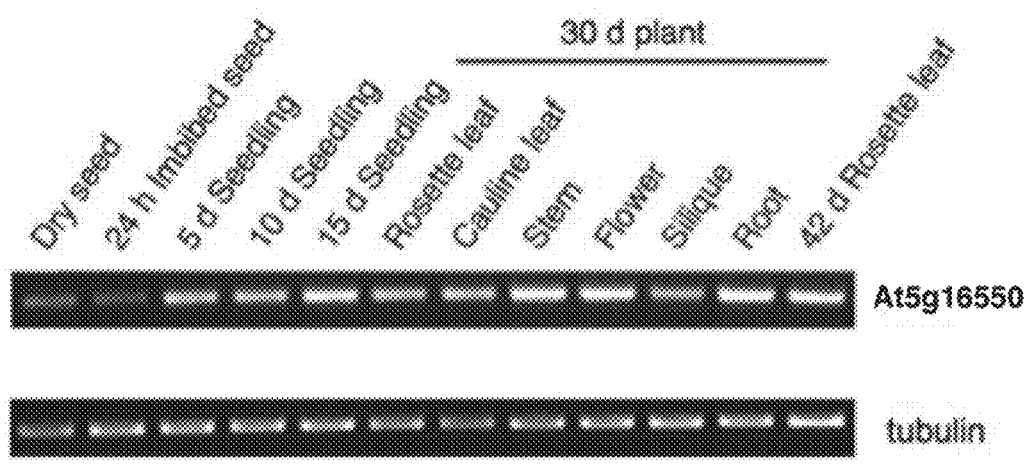
FIG. 4 shows At5g16550 expression in different *Arabidopsis* tissues, organs, and developmental stages.

FIG. 4 shows At5g16550 expression in *Arabidopsis*. RT-PCR analysis revealed that At5g16550 transcripts are detectable in a variety of *Arabidopsis* tissues/organs and developmental stages (as indicated by labels), including in the mature (dry) seed and germinating seed (i.e., 24 h post-imbibition), germinated seedlings, and in various vegetative tissue of 30-day-old plants, suggesting that the protein is a constitutive component of the LD proteome throughout the plant lifecycle. Endogenous tubulin was used as a reference gene in a parallel set of RT-PCRs. All RT-PCRs were performed using cDNA derived from isolated total RNA.

Figure 5:
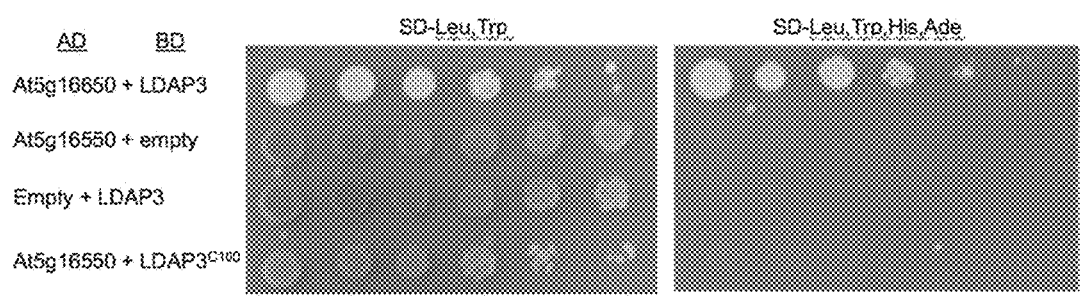
FIG. 5 shows the results of yeast two-hybrid assays for At5g16550 and LDAP3, and the LDAP3 mutant LDAP3$^{C100}$ along with empty vector controls.
Figure 6A:
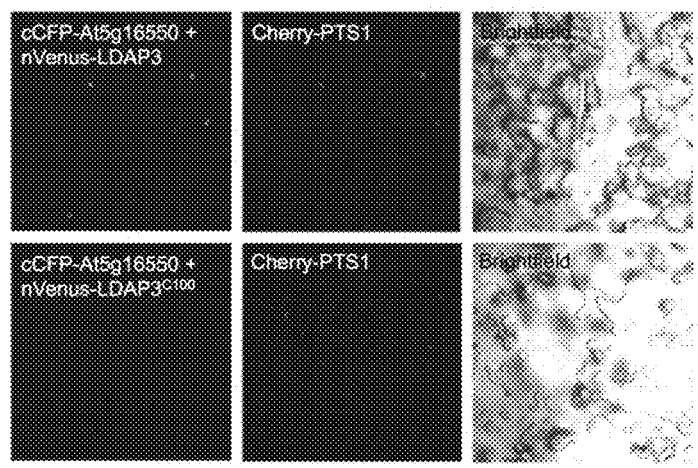
FIG. 6A shows CLSM images of the bimolecular fluorescence complementation (BiFC) of (co)transiently-expressed cCFP-tagged At5g16550 and nVenus-tagged LDAP3 or the LDAP3$^{C100}$ mutant along with an expressed Cherry-PTS1 transformation marker protein in tobacco leaf cells.
Figure 6B:
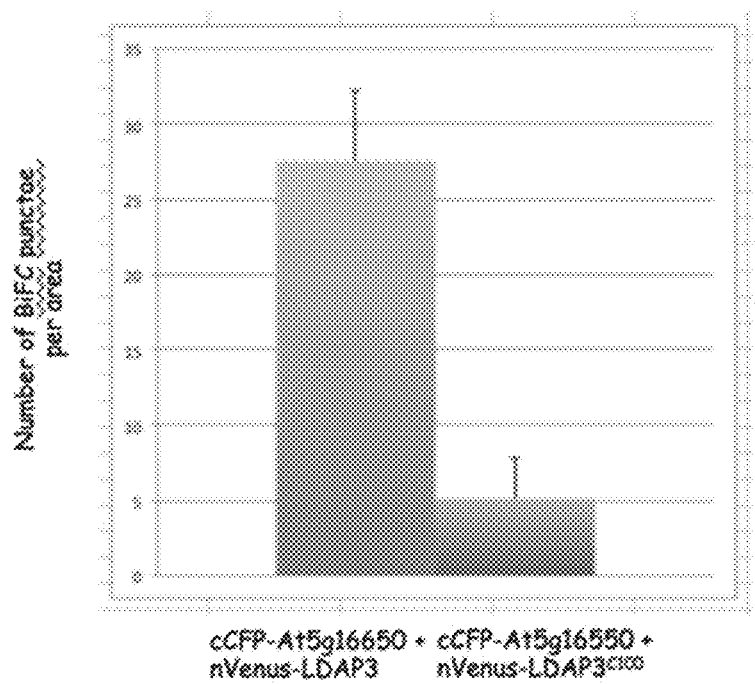
FIG. 6B shows the relative amounts of BiFC signal for cotransiently-expressed cCFP-At5g16550 and either nVenus-tagged LDAP3 or LDAP3$^{C100}$ in tobacco leaf cells.
Figure 6C:
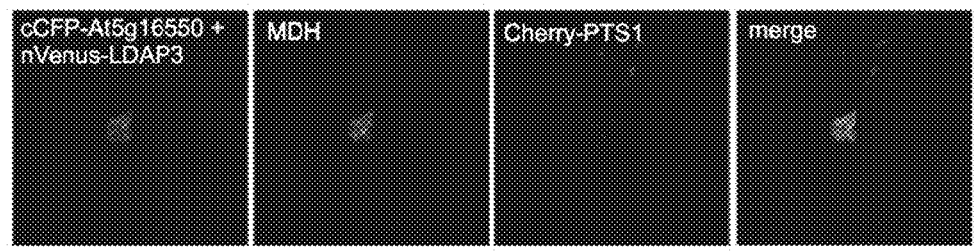
FIG. 6C shows CLSM images of the cCFP-At5g16550 and nVenus-LDAP3 BiFC fluorescence signal colocalized with MDH-stained cytoplasmic LDs in a transiently-transformed tobacco leaf cell.

FIGS. 5 and 6 show the interaction of At5g16550 and LDAP3 in yeast and plant cells. Yeast strains were co-transformed with indicated pairs of GAL4-activation domain (AD) and GAL4-binding domain (BD) fusion proteins or the corresponding empty BD or AD control plasmids and then spotted (as serial dilutions) onto agar plates containing either low-stringency (SD-Leu,Trp) or high-stringency media (SD-Leu,Trp,His,Ade), where cell growth is dependent on two-hybrid protein interaction. As shown in FIG. 5A, co-expression of AD-At5g16550 and BD-LDAP3, but not a mutant version of BD-LDAP3 (BD-LDAP3$^{C100}$), whereby the C-terminal 100 amino acid residues of the protein known to be necessary for targeting to LDs were removed (Gidda et al., 2016), resulted in significant yeast growth on high selection media, indicating that At5g16550 and LDAP3 interact. Consistent with these data, FIG. 6 shows the results of in vivo bimolecular fluorescence complementation (BiFC) assays indicating that At5g16550 and LDAP3 interact at LDs in plant cells. Tobacco leaves were co-infiltrated with binary vectors encoding the C-terminal half of the cyan fluorescent protein (cCFP) appended to At5g16550 and the N-terminal half of the Venus fluorescent protein (nVenus) appended to either full-length LDAP3 or LDAP3$^{C100}$. In addition, cells were transformed with a peroxisomal marker protein (consisting of Cherry fused to a type 1 peroxisomal targeting signal [Cherry-PTS1] (Ching et al., 2012), which was used to identify transformed cells and also served as an internal normalization for reconstituted BiFC, minimizing differences due to cell-to-cell variability in expression levels. Representative CLSM images (FIG. 6A) and quantifications of BiFC signal based on >25 leaf areas expressing Cherry-PTS1 from at least two separate infiltrations (FIG. 6B) revealed that cells co-transformed with cCFP-At5g16550 and nVenus-LDAP3 displayed significantly more BiFC (punctate) signal than cells co-transformed with LDAP3$^{C100}$. Further, higher magnified CLSM imaging of the cCFP-At5g16550 and nVenus-LDAP3 BiFC punctate (as seen in FIG. 6A), along with staining of LDs with the blue-fluorescent neutral lipid dye monodansylpentane (MDH), confirmed that the two proteins were interacting at LDs in plant cells (FIG. 6C).

EXAMPLE 3

Transgenic *Arabidopsis* at5g16550 Suppression Mutant Lines

Figure 7A:
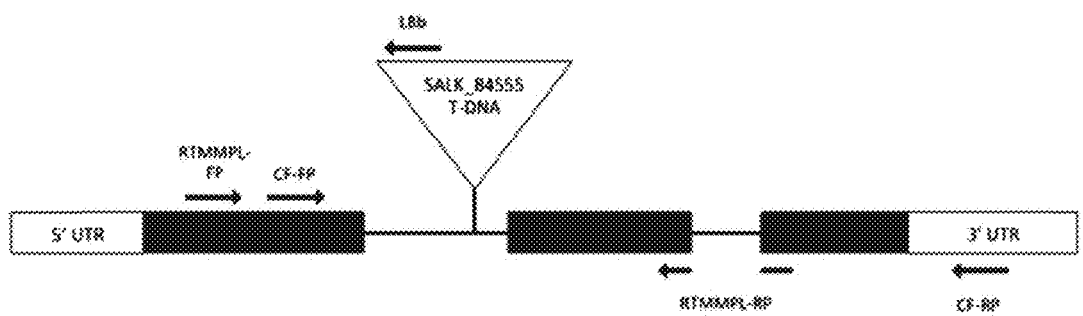
FIG. 7A shows T-DNA locations, zygosity, and At5g16550 transcript levels in the *Arabidopsis* at5g16550 knockdown (SALK_084555) mutant line.
Figure 7A:
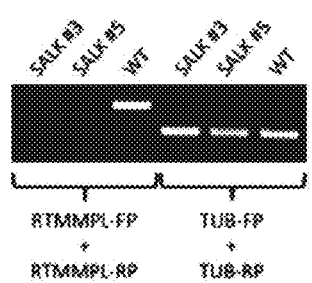
Figure 7B:
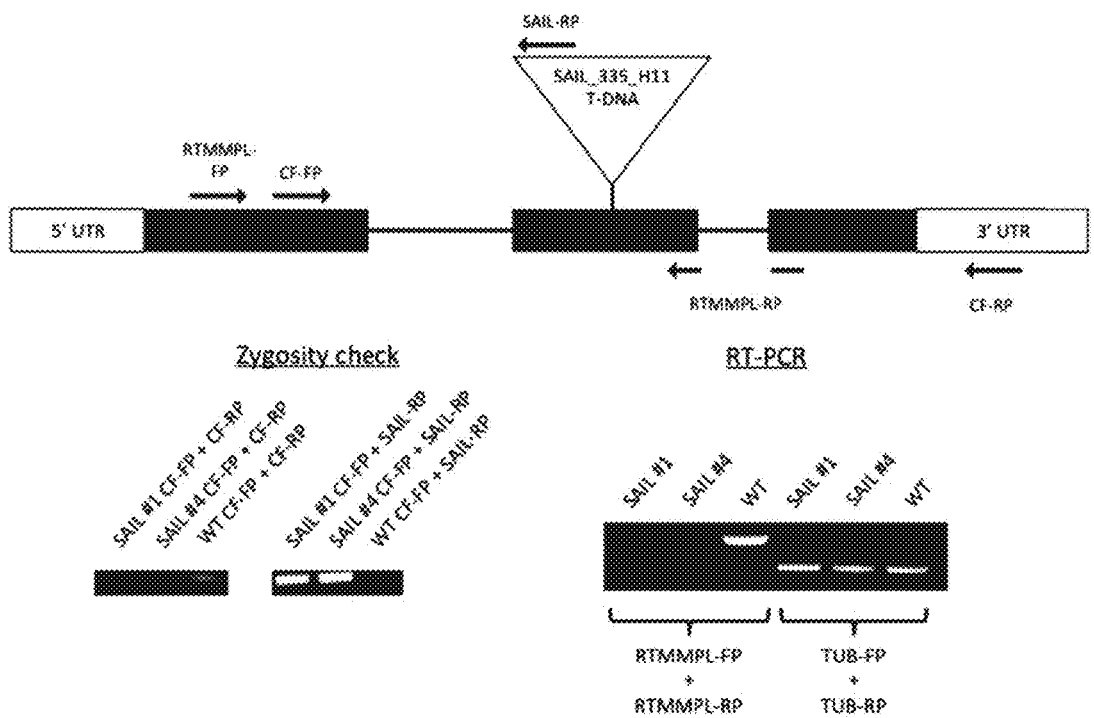
FIG. 7B shows T-DNA locations, zygosity, and At5g16550 transcript levels in the *Arabidopsis* at5g16550 knockout (SAIL_335_H11) mutant line.

Shown in FIG. 7 are the T-DNA locations, zygosity, and AT5G16550 transcript levels in the *Arabidopsis* at5g16550 knockdown (SALK_084555) (FIG. 7A) and knockout (SAIL_335_H11) (FIG. 7B) mutant lines obtained from the *Arabidopsis* Biological Resource Centre (ABRC). The schematic diagrams show the organization of the AT5G16550 gene, which is annotated by TAIR to contain three exons (represented by black bars), the second of which contains the T-DNA insert in the knockout line, and two introns, the first of which contains the T-DNA insert in the knockdown line. The relative positions of At5g16550-specific primer pairs are also shown in each diagram as black arrows. Two independent lines for each mutant (i.e., SALK #3 and #5; SAIL #1 and #4) were confirmed to be homozygous, as evidenced by the PCR screening results (see 'Zygosity check'). Ethidium bromide-stained agarose gels revealed that PCR amplicons were not generated when using gene-specific primers CF-FP and CF-RP, which flank the location of the T-DNA insert. Conversely, using wild-type (WT) DNA, the same primers generated an amplicon of a specific size due the absence of a T-DNA. The location of the T-DNA was also confirmed in the two plants using a T-DNA-specific primer (LBb or SAIL-RP) and the At5g16550 gene-specific primer CF-FP. As shown under 'RT-PCR', a reduction or apparent lack of full-length AT5G16550 transcript levels was observed in both sets of lines (i.e., SALK #3 and #5; SAIL #1 and #4) compared to wild-type levels using primers RT MMPL-FP and RT MMPL-RP. Primers designed for the amplification of endogenous α-tubulin transcripts were used as a control. Taken together, these results confirm that SALK_084555 and SAIL_335_H11 are bona fide at5g16550 knockdown and knockout *Arabidopsis* mutant lines, respectively.

EXAMPLE 4

Figure 8A:
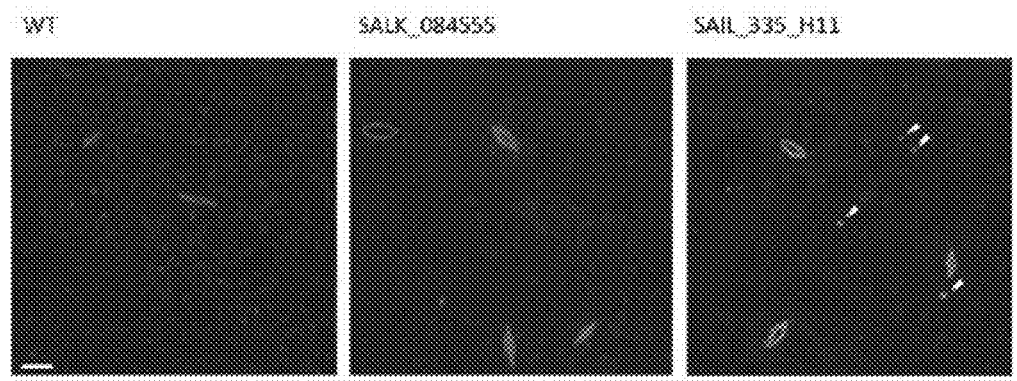
FIG. 8A shows CLSM micrographs of LDs stained with BODIPY 493/503 along with chlorophyll autofluorescence of 15 day-old leaves from WT and at5g16550 suppression mutant lines (SALK_084555 [knockdown] and SAIL_335_H11 [knockout]) at the end of the night, when LD abundance is high in WT, with arrowheads highlighting examples of enlarged lipid droplets in the knockout mutant leaves.
Figure 8B:
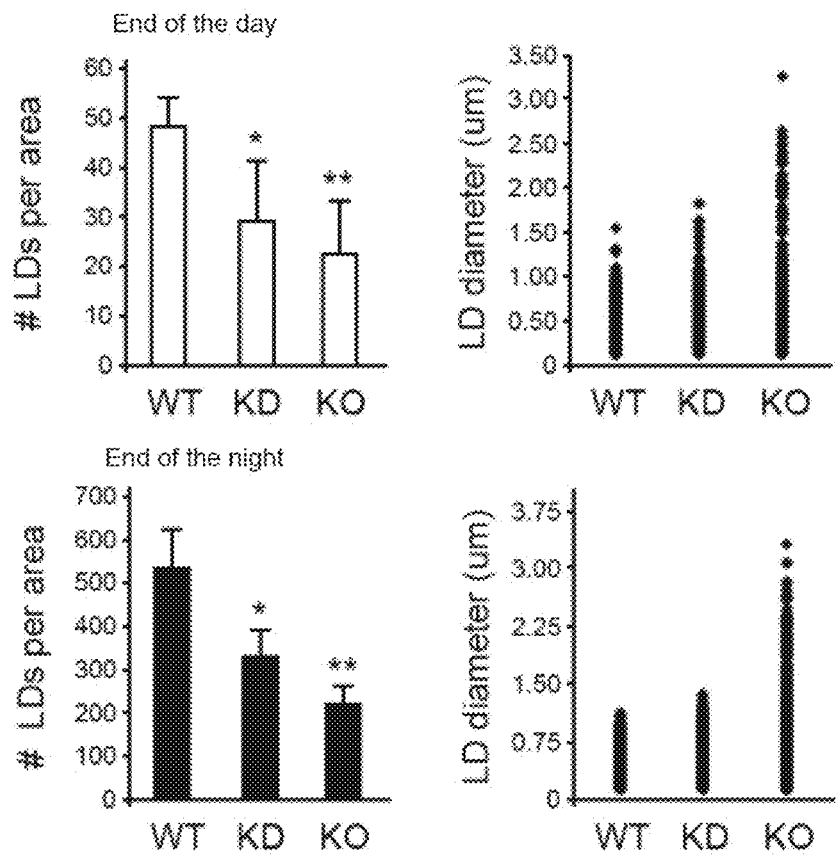
FIG. 8B shows quantification of number and sizing of LDs in 15 day-old leaves from wild-type (WT) and the at5g16550 knockdown (SALK_084555) and knockout (SAIL_335_H11) at the end of day or the end of the night.

Increased LD Size Heterogeneity and Neutral Lipid Content in Leaves in AT5G16650 Suppression Mutant Lines As shown in FIG. 8, LD size and abundance in leaves are affected in transgenic *Arabidopsis* At5g16550 suppression mutant lines. Leaves of 15-day-old WT, At5g16550 suppression mutant (SALK_084555), and At5g16550 knockout mutant (SAIL_335_H11) plants were formaldehyde fixed at the end of the dark cycle, when LD abundance is highest in WT plants (Gidda et al., 2016), then LDs were stained with BODIPY 493/503 and imaged (along with chlorophyll autofluorescence), using CLSM, as described elsewhere (Cai et al., 2015; Gidda et al., 2016). Representative micrographs are shown in FIG. 8A, and LD numbers and sizes for each line (n=9) at both end of the night and end of the day, when LD abundance is highest and lowest in WT plants, respectively (Gidda et al., 2016), were quantified using ImageJ according to Cai et al. (2015) (FIG. 8B). Arrowheads in the representative micrograph of the knockout mutant (FIG. 8A, right panel) highlight the presence of several 'supersized' LDs, which were not observed in leaves of WT or the knockdown mutant. Consistent with these observations, quantification of LD size and abundance (see corresponding graphs in FIG. 8B) revealed that while the total number of LDs in the knockdown and knockout mutants at both the end of day and end of the night was significantly lower than that of the WT (i.e., ~28 and 23 versus 48, and ~340 and 210 versus 510; compare y-axes), the number of LDs with diameters greater than the average LD diameter in WT was significantly greater in the knockout mutant. That is, the sizes of LDs in the knockout mutant ranged from the typical 0.2 μm seen in WT (and knockdown plants) at the end of the day and end of the night to over 1.6 μm.

Figure 9A:
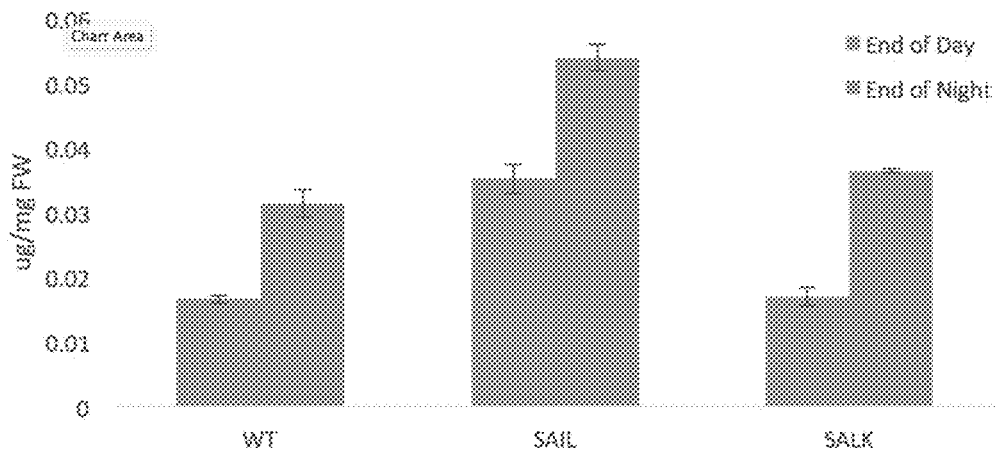
FIG. 9A shows quantification of neutral lipid content in 15 day-old leaves from WT and at5g16550 suppression mutant lines (SALK_084555 [knockdown] and SAIL_335_H11 [knockout]) at the end of the day and end of the night as indicated.
Figure 9B:
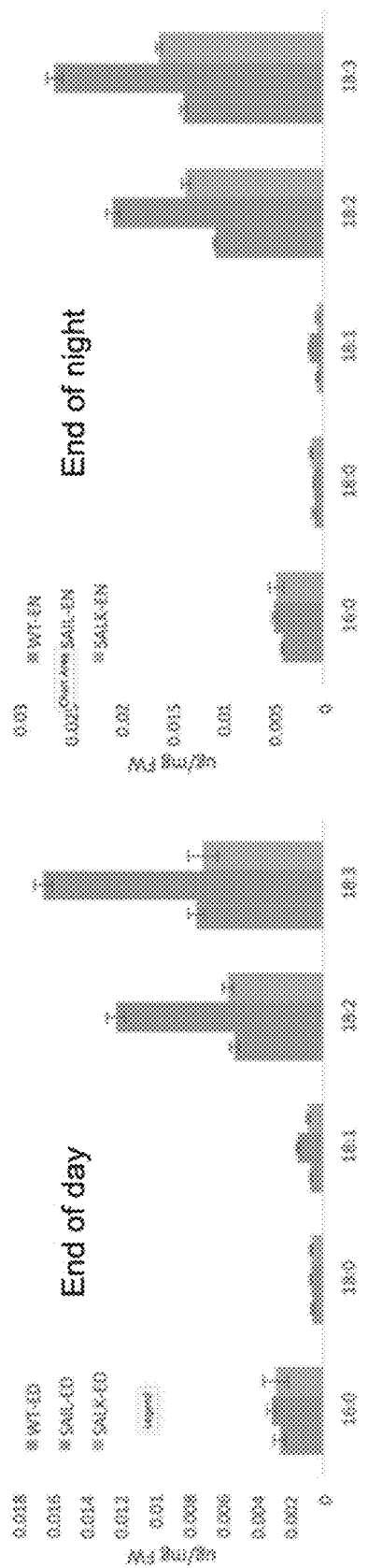
FIG. 9B shows quantification of fatty acid composition in 15 day-old leaves from WT and at5g16550 suppression mutant lines (SALK_084555 [knockdown] and SAIL_335_H11 [knockout]) at the end of the day and end of the night.

FIG. 9 shows an analysis of neutral lipid and fatty acid content in 15-day old WT and at5g16550 suppression mutant lines (i.e., SALK_084555 [knockdown] and SAIL_335_H11 [knockout]) at the end of the night and end of the day, when as already mentioned, LD abundance is highest and lowest, respectively in WT plants (Gidda et al., 2016). Briefly, five biological replicates of leaf material were weighed and flash frozen, then total lipids were extracted from the tissue using a hexane/isopropanol method. Neutral lipids were subsequently isolated by solid-phase extraction and analyzed by gas chromatograpy and flame ionization detection. Values represent average and standard deviation; *$p<0.05$. Note the relative increase in neutral lipid content in both the knockdown and knockout at5g16550 mutant lines compared to WT at both the end of the day and end of the night (FIG. 9A), due primarily to increases in polyunsaturated (i.e., 18:2 and 18:3) fatty acids (FIG. 9B). Taken together and with those presented above, these data indicate that At5g16550 plays an important role in LD biogenesis (i.e., number and size) and also the accumulation of total neutral lipids in leaves.

EXAMPLE 5

Increased LD Size and Seed Oil Content in at5g16650 Suppression Mutant Lines

Suppression of At5g16550 gene expression results in the presence of abnormally large LDs in seeds and an increase in total seed oil content. FIG. 10A shows representative, CLSM images of BODIPY-stained LDs in WT, SAIL_335_H11 (knockout) and SALK_084555 (knockdown) mature, dry *Arabidopsis* seeds. Briefly, seeds were imbibed in deionized water for 20 minutes and the embryos were rolled out of the seed coats with a cover slip and imaged via CLSM. Note the presence of grossly enlarged, 'supersized' LDs in both the knockout and knockdown mutant lines (refer to arrowheads). LDs of this size are not seen in WT seeds. These data reveal a novel role for At5g16550 in the biogenesis and/or stability of LDs in seeds.

FIG. 10B shows an analysis of seed oil content and composition. Five biological replicates of seeds were weighed, then fatty acid methyl esters were prepared using methanolic-HCl, then the content and composition of seed oil was determined using GC-FID and tri-heptadecanoin as an internal standard. Values represent average and standard deviation; *$p<0.05$. Note the increase in total seed oil content in both knockout and knockdown lines, with increases in stoichiometric amounts of nearly all fatty acid components of seed oil. Taken together and with those presented above, these data indicate that At5g16550 plays an important role not only in determining the cellular properties of LD in seeds, but also the accumulation of total oil within developing seeds.

FIG. 11 shows that seed oil breakdown is moderately affected in At5g16550 mutant seeds and correlates with the presence of abnormally large LDs during post-germinative growth. FIG. 11A shows representative, CLSM images of BODIPY-stained LDs in WT, SAIL_335_H11 (knockout) and SALK_084555 (knockdown) in *Arabidopsis* seedlings 1, 2 and 4 days after germination (shown in top, middle and bottom row of micrographs, respectively). Note the persistence of 'supersized' LDs in the knockdown mutant line at 2 and 4 days after germination (middle and bottom rows of micrographs, respectively). FIGS. 11B and 11C show an analysis of seed oil content and composition. Five biological replicates of seedlings were weighed, then fatty acid methyl esters were prepared using methanolic-HCl, then the content and composition of seed oil was determined using GC-FID and tri-heptadecanoin as an internal standard. Values represent average and standard deviation; *$p<0.05$ (n=3). In FIG. 11B the increase in total seed oil content in both knockout and knockdown lines in mature seeds and seedlings occurred one day after germination, but only in the knockdown line 2 and 4 days after germination. Similarly, there were increases in stoichiometric amounts of nearly all fatty acid components of seed oil in both the knockdown and knockout seedlings 1, 2 and 4 days after germination.

The results discussed above show that *Arabidopsis* At5g16550 is a plant-specific protein (FIG. 1), containing an MMPL domain (FIG. 2), that was identified as an interacting protein with the LDAP isoform 3 (FIGS. 5 and 6), and localizes to LDs of plant cells (FIG. 3). The At5g16550 gene was expressed in all *Arabidopsis thaliana* (plant) tissues examined (FIG. 4). Two mutants were identified with reduced or no expression (FIG. 7), and these mutants had fewer but substantially larger lipid droplets in plant leaves (FIG. 8) and increased neutral lipid content (FIG. 9), suggesting that the At5g16550 protein may function to regulate LD size, abundance, and neutral lipid content in plants. Likewise, in dry seed cells of these mutants, there were also larger lipid droplets visible, and there was significantly more total lipid in these mutant seeds (FIG. 10), as well as at several stages of post-germinative seedling growth (FIG. 11). Given that genes similar to At5g16550 are easily identified in several commercially-important oilseed crops (FIG. 12), and that *Arabidopsis thaliana* has been used as, and is accepted as, a representative plant system for oilseed crops (Wallis and Brown, 2010; Li-Beisson et al, 2013), this demonstrates that loss-of At5g16550-like gene function should increase the oil content in tissues of oil crops, like canola, Camelina, soybean, sunflower, safflower, cotton, palm, coconut, peanut, and others.

REFERENCES CITED

The following references, to the extent that they provide exemplary procedural or other details supplementary to those set forth herein, are specifically incorporated herein by reference.

Cai Y, Goodman J M, Pyc M, Mullen R T, Dyer J M, Chapman K D. 2015. *Arabidopsis* SEIPIN proteins modulate triacylglycerol accumulation and influence lipid droplet proliferation. Plant Cell. 27: 2616-2636.

Ching S L, Gidda S K, Rochon A, van Cauwenberghe O R, Shelp B J, Mullen R T. 2012. Glyoxylate reductase isoform 1 is localized in the cytosol and not peroxisomes in plant cells. J. Integr. Plant Biol. 54: 152-168.

Converse S E, Mougous J D, Leavell M D, Leary J A, Bertozzi C R, Cox J S. 2003. MmpL8 is required for sulfolipid-1 biosynthesis and *Mycobacterium tuberculosis* virulence. Proc. Natl. Acad. Sci. USA. 100: 6121-6126.

Divi U K, Zhou X R, Wang P, Butlin J, Zhang D M, Liu Q, Vanhercke T, Petrie J R, Talbot M, White R G, Taylor J M, Larkin P, Singh S P. 2016. Deep sequencing of the fruit transcriptome and lipid accumulation in a non-seed tissue of Chinese Tallow, a potential biofuel crop. Plant Cell Physiol. 57: 125-137

Gidda S K, Park S, Pyc M, Yurchenko O, Cai Y, Wu P, Andrews D W, Chapman K D, Dyer J M, Mullen R T. 20-16. Lipid droplet-associated proteins (LDAP5) are required for the dynamic regulation of neutral lipid compartmentation in plant cells. Plant Physiol. 170: 2052-2071.

Horn P J, James C N, Gidda S K, Kilaru A, Dyer J M, Mullen R T, Ohlrogge J B, Chapman K D. 2013. Identification of a new class of lipid droplet-associated proteins in plants. Plant Physiol. 162: 1926-1936.

Koornneef M, Meinke D. 2010. The development of *Arabidopsis* as a model plant. Plant J. 61: 909-921.

Li-Beisson Y, Shorrosh B, Beisson F, Andersson M X, Arondel V, Bates P D, Baud S, Bird D, Debono A, Durrett T P, Franke R B, Graham I A, Katayama K, Kelly A A, Larson T, Markham J E, Miguel M, Molina I, Nishida I, Rowland O, Samuels L, Schmid K M, Wada H, Welti R, Xu C, Zallot R, Ohlrogge J. 2013. Acyl-lipid metabolism. *Arabidopsis* Book. 11:e0161. doi: 10.1199/tab.0161.

McCartney A W, Greenwood J S, Fabian M R, White K A, Mullen R T. 2005. Localization of the tomato bushy stunt virus replication protein p33 reveals a peroxisome-to-endoplasmic reticulum sorting pathway. Plant Cell. 17: 3513-3531.

Pacheco S A, Hsu F F, Powers K M, Purdy G E. 2013. MmpL11 protein transports mycolic acid-containing lipids to the mycobacterial cell wall and contributes to biofilm formation in *Mycobacterium smegmatis*. J. Biol. Chem. 288:24213-24222

Petrie J R, Shrestha P, Liu Q, Mansour M P, Wood C C, Zhou X R, Nichols P D, Green A G, Singh S P. 2010. Rapid expression of transgenes driven by seed-specific constructs in leaf tissue: DHA production. Plant Methods. 6:8.

Provart N J, Alonso J, Assmann S M, Bergmann D, Brady S M, Brkljacic J, Browse J, Chapple C, Colot V, Cutler S, Dangl J, Ehrhardt D, Friesner J D, Frommer W B, Grotewold E, Meyerowitz E, Nemhauser J, Nordborg M, Pikaard C, Shanklin J, Somerville C, Stitt M, Torii K U, Waese J, Wagner D, McCourt P. 2016. 50 years of *Arabidopsis* research: highlights and future directions. New Phytol. 209: 921-944.

Tekaia F, Gordon S V, Garnier T, Brosch R, Barrell B G, Cole S T. 1999. Analysis of the proteome of *Mycobacterium tuberculosis* in silico. Tuber Lung Dis. 79: 329-342.

Varela C, Rittmann D, Singh A, Krumbach K, Bhatt K, Eggeling L, Besra G S, Bhatt A. 2012. MmpL genes are associated with mycolic acid metabolism in mycobacteria and corynebacteria. Chem. Biol. 19: 498-506.

Viljoen A, Dubois V, Girard-Misguich F, Blaise M, Herrmann J L, Kremer L. 2017. The diverse family of MmpL transporters in mycobacteria: from regulation to antimicrobial developments. Mol Microbiol. March 24. doi: 10.1111/mmi.13675. [Epub ahead of print]

Wallis J G, Browse J. 2010. Lipid biochemists salute the genome. Plant J. 61: 1092-1106.

What is claimed is:

1. A method for producing a modified plant having increased oil content or increased cytoplasmic lipid droplet volume in cells of the plant compared to an unmodified plant of the same species, comprising:
   introducing a mutation into a gene in cells of a plant, wherein the gene is At5g16550 or a homolog thereof, wherein the gene encodes a protein containing a mycobacterial membrane protein large (MMPL) like domain, and wherein the mutation results in reduced or eliminated expression of the protein encoded by At5g16550 or a homolog thereof.

2. The method of claim 1, wherein the protein is encoded by At5g16550 and has a sequence comprising SEQ ID NO:1.

3. The method of claim 1, wherein the plant is an *Arabidopsis* plant.

4. The method of claim 1, wherein the plant is a canola, Camelina, soybean, sunflower, safflower, cotton, palm, coconut, or peanut plant.

5. A modified plant having increased oil content or increased cytoplasmic lipid droplet volume in cells of the plant compared to an unmodified plant of the same species, wherein cells of the plant comprise a mutation in a gene found in the cells of the plant, wherein the gene is a homolog of At5g16550, wherein the gene encodes a protein containing a mycobacterial membrane protein large (MMPL) like domain, and wherein the mutation results in reduced or eliminated expression of a protein encoded by a homolog of At5g16550.

6. A seed of the modified plant of claim 5, wherein the seed comprises the mutation.

* * * * *

UNITED STATES PATENT AND TRADEMARK OFFICE
CERTIFICATE OF CORRECTION

PATENT NO. : 10,308,950 B2
APPLICATION NO. : 15/624495
DATED : June 4, 2019
INVENTOR(S) : Kent Chapman et al.

Page 1 of 1

It is certified that error appears in the above-identified patent and that said Letters Patent is hereby corrected as shown below:

In the Specification

Column 1, First Paragraph, Lines 5-10, delete "This application claims priority to U.S. Provisional Patent Application Ser. No. 62/350,843, entitled "Methods for Increasing Oil content in Plant Tissues by Suppressing Hydrophobic Lipid Droplet Protein," filed on Jun. 16, 2016, the entire contents of which are hereby incorporated by reference." and insert -- This invention was made with government support under DE-SC0000797 awarded by the Department of Energy. The government has certain rights in the invention. This application also claims priority to U.S. Provisional Patent Application Serial No. 62/350,843, entitled "Methods for Increasing Oil Content in Plant Tissues by Suppressing Hydrophobic Lipid Droplet Protein," filed on June 16, 2016, the entire contents of which are hereby incorporated by reference. --, therefor.

Signed and Sealed this
Twenty-fourth Day of November, 2020

Andrei Iancu
*Director of the United States Patent and Trademark Office*